United States Patent [19]

Marquez et al.

[11] Patent Number: 5,817,799
[45] Date of Patent: Oct. 6, 1998

[54] 2'-FLUOROFURANOSYL DERIVATIVES AND METHODS FOR PREPARING 2'-FLUOROPYRIMIDINE AND 2'-FLUOROPURINE NUCLEOSIDES

[75] Inventors: Victor E. Marquez, Bethesda; John S. Driscoll, Rockville; Ronald J. Wysocki, Jr., Potomac; Magbool A. Siddiqui, Gaithersburg, all of Md.

[73] Assignee: The United States of America as represented by the Department of Health and Human Services, Washington, D.C.

[21] Appl. No.: 556,713

[22] Filed: Jul. 23, 1990

[51] Int. Cl.$^6$ ........................................... C07H 1/00
[52] U.S. Cl. .................... 536/28.2; 536/27.1; 536/27.11; 536/27.13; 536/27.21; 536/27.6; 536/27.8; 536/27.81; 536/28.1; 536/28.5; 536/28.53; 536/28.54
[58] Field of Search .................. 536/23, 24, 27, 536/28, 29, 27.1, 27.11, 27.13, 27.21, 27.6, 27.8, 27.81, 28.1, 28.5, 28.53, 28.54, 28.2

[56] References Cited

U.S. PATENT DOCUMENTS

| | | | |
|---|---|---|---|
| 4,211,773 | 7/1980 | Lopez et al. | 536/23 |
| 4,751,221 | 6/1988 | Watanabe et al. | 536/24 |
| 4,908,440 | 3/1990 | Sterzycki et al. | 536/23 |
| 4,973,677 | 11/1990 | Sterzycki et al. | 536/24 |
| 5,594,124 | 1/1997 | Chou | 536/28.4 |
| 5,648,473 | 7/1997 | Chou | 536/18.4 |
| 5,691,319 | 11/1997 | Kaneko et al. | 536/28.1 |

OTHER PUBLICATIONS

Tann et al, J. Org. Chem. 50:3644–3647 (1985).
Marquez et al, J. Med. Chem. 33:978–985 (1990).

*Primary Examiner*—James O. Wilson
*Attorney, Agent, or Firm*—Morgan & Finnegan, L.L.P.

[57] ABSTRACT

A method of preparing a 2'-fluoro compound of the formula

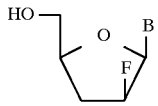 (I)

where B is selected from the group consisting of purines and pyrimidines, both of which may be substituted, comprises reacting a compound of the formula II(a) or II(b)

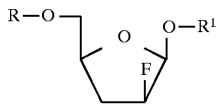

(IIa)

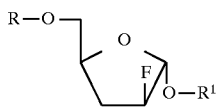

(IIb)

where R and R' are as defined in the specification with an acid halide under conditions effective to obtain a halide of the formula

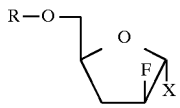 (III)

where X is a halogen. A silane of the formula B-Si (R")$_3$ where R" is as defined in the specification, is added to this product (III) under conditions effective to obtain a compound of the formula (IV)

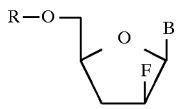

(IV)

The compound of formula (IV) is reacted with a reagent selected from the group consisting of ammonia, BCl$_3$ and ((C$_1$–C$_{10}$)alkyl)$_4$ NF, under conditions effective to obtain the compound of formula (I). The compounds of formula (I) resulting from these methods exhibit anti-HIV activities and are useful for therapy against the HIV virus.

6 Claims, No Drawings

2'-FLUOROFURANOSYL DERIVATIVES AND METHODS FOR PREPARING 2'-FLUOROPYRIMIDINE AND 2'-FLUOROPURINE NUCLEOSIDES

FIELD OF THE INVENTION

This invention relates to 2'-fluoroarabinofuranosyl compounds which are intermediates in the preparation of 2',3'-dideoxy-2'-fluoroarabinosyl nucleosides. This invention also relates to a novel method of synthesizing known 2'-fluoropyrimidine and 2'-fluoropurine nucleosides.

BACKGROUND OF THE INVENTION

Acquired immunodeficiency syndrome, or AIDS, is a fatal disease which has reached epidemic proportions among certain high risk groups. Several features of AIDS make therapy extremely difficult. The main target of the AIDS virus, now known as HIV, or human immunodeficiency virus, is the T4 lymphocyte, a white blood cell that marshals immunodefenses. The virus depletes T4 cells. This depletion in AIDS causes a severe depression of the immune response. Thus, to be effective against AIDS any drug must modify virus effect without much help from host immunity. Furthermore, the virus also affects cells in the central nervous system, where it is protected by the blood-brain barrier from compounds that might otherwise be effective against the virus. In infecting its host, the HIV binds to specific cell-surface receptor molecules. The virus penetrates the cell cytoplasm and sheds its protein coat, thereby releasing its genetic material, a single strand of RNA. A viral enzyme, reverse transcriptase, accompanies the RNA. The virus, a retrovirus, thereby transcribes the RNA into DNA. Ultimately, some DNA copies of the HIV genome become integrated into the chromosomes of the host cell.

The integrated viral genome, known as a provirus, may remain latent until the host cell is stimulated, such as by another infection. The proviral DNA is then transcribed into mRNA, which directs the synthesis of viral proteins. The provirus also gives rise to other RNA copies that will serve as the genetic material of viral progeny. The proteins and the genomic RNA congregate at the cell membrane and assemble to form new HIV particles, which then break off from the cell. Two HIV genes, tat and trs/art, appear to control this burst of replication, which destroys the cell. These genes code for small proteins that boost the transcription of proviral DNA and the synthesis of viral proteins.

Several compounds have been shown to reduce the activity of reverse transcriptase in vitro. Reverse transcription is a step that is essential to viral replication but irrelevant to host cells. It has been found that HIV replication is considerably slower in the presence of compounds such as suramin, antimoniotungstate, phosphonoformate, and a class of nucleoside analogues known as dideoxynucleosides.

Nucleoside analogues are a class of synthetic compounds that resemble the naturally occurring nucleosides, which are chemical precursors of DNA and RNA. A nucleoside comprises a single or double-ring base linked to a five-carbon sugar molecule. An analogue differs from the naturally-occurring nucleoside in large or small features of the base or the sugar. An enzyme that normally acts on a nucleoside in the course of viral replication may also bind to a nucleoside analogue. Because the naturally occuring nucleosides and nucleoside analogues differ, however, binding to the analogue can incapacitate the enzyme and disrupt a molecular process crucial to viral replication.

Of the synthetic nucleoside analogues, dideoxyadenosine (ddA) has been found to have potent in vitro activity against the human immunodeficiency virus which causes AIDS. The activated form of the dideoxynucleosides, their 5'-triphosphates, appear to inhibit replication of the virus at the stage of reverse transcription of de novo infection of the virus. Due to this, it is most likely that a drug of this type must be taken continuously if its therapeutic effect is to be maintained. Since daily treatments may extend over long periods of time, oral drug administration is envisioned as the most practical route for patient populations.

Drugs administered orally are exposed to pH ranges of 1 to 2 in the human stomach environment for approximately one hour. In the case of ddA this may provide for drug instability, since this compound undergoes acid-catalyzed hydrolysis of its glycosidic bond at a rate 40,000 times faster than adenosine. ddA has a $t_{1/2}$ of 35 seconds at a pH=1.0 at 37° C. Cleavage of this compound thus not only reduces its efficacy, but potential problems of toxicity may occur due to formation of excessive quantities of one of its cleavage products.

2'-F-substituted dideoxynucleoside derivatives of dideoxyadenosine (ddA) were originally disclosed in 1987 (Marquez et al, Biochem. Pharmacol. 36(17):2719–2722 (1987); U.S. patent application Ser. Nos. 07/039,402, filed Apr. 17, 1987 and 07/288,652, filed Dec. 12, 1988). Among the disclosed compounds are 6-amino-(β'D-2',3',dideoxy-2'-fluororibofuranosyl)-9-H-purine or 2'-F(ddA) and 6-amino-9-(β-D-2',3'-dideoxy-2'-fluoroarabinofuransyl)-9H-purine or 2'-F-ara-ddA.

The first compound was obtained from 3'-deoxy-ara-A by a four-step process involving protecting the 5'-hydroxyl group with dimethoxytrityl chloride, activating the 2'-hydroxyl group by forming the corresponding triflate, inverting the configuration at the 2'-position by a $Sn_2$ displacement using tetra-n-butyl ammonium fluoride, and removing the dimethoxytrityl protective group using dichloroacetic acid.

The second compound was prepared by condensing 6-chloropurine with 3-O-acetyl-5-O-benzoyl-2-deoxy-2-fluoro-D-arabinofuranosyl bromide, separating the expected four isomers produced, characterizing the correct 6-chloroisomer, and subjecting this isomer to ammonolysis with concentrated methanolic ammonia to give 6-amino-9-(β-D-2'deoxy-2'-fluoroarabinofuranosyl)-9H-purine or 2'-F-ara-dA. The selective protection of the 5'-hydroxyl function of this compound with t-butyl dimethylsilyl chloride yielded a product permitting a 2-step reduction of the 3'-hydroxy group. Further treatement with phenylchlorothionocarbonate, followed by reduction of the intermediate 3'-O-phenoxy-thiocarbonyl derivative with tri-n-butyltin hydride produced the desired 2',3'-dideoxy nucleoside. The 5'-blocking group was then removed with tetra-n-butyl ammonium fluoride to yield 2'-F-ara-ddA.

The latter compound has the fluorine stereochemically placed in the β configuration at the 2'-position, or up, and is as potent an anti-HIV compounds as ddA in the HIV/ATH8 test system. The earlier compound has the fluoride at the 2'-position in the α configuration, or down, however, and it affords only about 13% of the protection that ddA exhibits against HIV. It also is more toxic than ddA.

U.S. Pat. No. 4,625,020 to Brundidge et al discloses a method of producing 1-halo-2-deoxy-2-fluoroarabinofuranosyl derivatives bearing protective ester groups from 1,3,5-tri-O-acyl-ribofuranose. The 1-halo derivatives are intermediates in the synthesis of therapeutically active nucleosidic compounds.

EP Laid Open Application No. 010,205 discloses 5-substitued 1-(2'-deoxy-2'-substituted-β-D- arabinofuranosyl) pyrimidine nucleosides where the 2'-substituent is halogen, alkylsulfonyl or arylsulfonyl.

U.S. Pat. No. 4,908,440 to Sterzycki et al discloses other 2'-3'-dideoxy-2'-fluoronucleosides and 2',3'-dideoxy-2',3-didehydro-2'-fluoroneucleosides which are useful for anti-HIV therapy and a method for their preparation. The synthesis scheme shown on columns 1 and 2, Scheme I, bears some similarity to that of the invention. However, in this scheme no fluorine atom is on the ring and there is no obvious way of making the 2'-fluoro (alpha or beta) derivative of the compound 1 of this scheme.

DISCLOSURE OF THE INVENTION

This invention relates to a compound of the formula

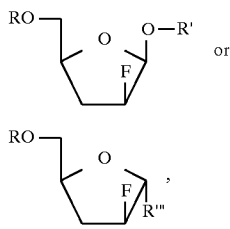

wherein

R is selected from the group consisting of H, $(C_7-C_{20})$ aroyl, $(C_6-C_{20})$aryl, alkylaryl and arylalkyl, and $(C_1-C_{10})$ alkyl-di$(C_6-C_{20})$aryl Si;

R' is selected from the group consisting of H, $(C_1-C_{10})$ alkyl, $(C_{7-20})$aroyl and $(C_2-C_{12})$acyl; and R''' is selected from the group consisting of halogen, $(C_1-C_{10})$alkoxyl, $(C_{1-C10})$acyloxy, O-methane-sulfonyl and O-p-toluene sulfonyl.

These compounds are useful in the preparation of 2',3'-dideoxy-2'-fluoroarabinofuranosyl pyrimidines and purines which have anti-HIV activities.

Also part of this invention is a method of preparing a 2'-fluoro compound of the formula

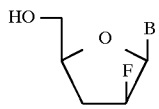

wherein B is selected from the group consisting of purines and pyrimidines, both of which may be substituted with halogen, $(C_1-C_{10})$alkyl, $(C_{1-C12})$ haloalkyl, haloalkylene and haloakynyl, amino, hydroxy, hydroxylamino, aminoxy, $(C_1-C_{10})$alkoxy, oxygen, mercapto, $(C_1-C_{10})$alkylmercapto, $(C_6-C_{20})$aryl, $(C_7-C_{20})$benzyloxy, $(C_1-C_{10})$alkylamino, aza, and cyano, the method comprising (a) reacting a compound of the formula

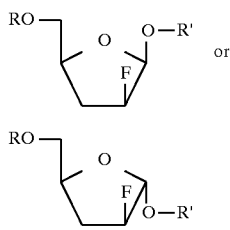

wherein

R is selected from the group consisting of H, $(C_7-C_{20})$ aroyl, $(C_6-C_{20})$aryl, alkylaryl and arylalkyl, and $(C_1-C_{10})$ alkyl-di$(C_6-C_{20})$aryl Si; and R' is selected from the group consisting of H, $(C_1-C_{10})$ alkyl, $(C_7-C_{20})$aroyl and $(C_2-C_{12})$acyl, all of which may be further substituted with O, S, N or alkyl, with an acid halide under conditions effective to obtain a halide of the formula

wherein X is selected from the group consisting of F, Cl, Br or I;

(b) adding thereto a silane of the formula

wherein

B is as defined above, and

R'' is, independent of one another, selected from the group consisting of $(C_1-C_{10})$alkyl, $(C_6-C_{20})$aryl and di$(C_1-C_{10})$ alkyl-$(C_6-C_{20})$aryl under conditions effective to obtain a compound of the formula

wherein R and B are as defined above; and (c) reacting the compound of formula (IV) with a reagent selected from the group consisting of ammonia/methanol, $Bu_4NF$, $BCl_3$, sodium hydroxide and diisopropylamine under conditions effective to obtain the compound of formula (I).

PREFERRED EMBODIMENTS OF THE INVENTION

This invention arose from a desire by the inventors to provide a novel method of preparing 2'-fluoro-dideoxy-pyrimidines and 2'-fluoro-dideoxy-purines which are useful for therapy against the HIV virus.

Conventional syntheses of 2'-fluoro-dideoxy nucleosides reported thus far require a final reduction step to remove the 3'-hydroxyl after the condensation of the sugar with the base (aglycon) (e.g., U.S. Pat. No. 4,908,440 to Sterzycki et al, paragraph bridging columns 6 and 7). These reductions are difficult and inefficient and must be performed on every nucleoside analogue synthesized.

The use of the novel method described herein provides the following advantages.

(a) Analogue synthesis is greatly facilitated since the reduction is performed before the condensation reaction, requiring the use of the reduction only once for the production of many compounds rather than every time the new compound is prepared.

(b) The low yield reduction occurs early in the reaction sequence rather than at the end, providing a more efficient synthesis technique from the standpoint of overall yield and economy.

In the course of developing a novel method, the inventors not only attained such a goal but, in addition, are providing novel intermediate compounds not previously known in the art.

Thus, this invention provides a compound of the formula

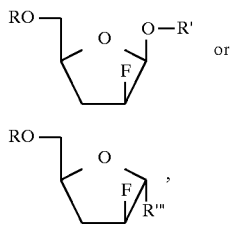

wherein

R is selected from the group consisting of H, $(C_7-C_{20})$ aroyl, $(C_6-C_{20})$aryl, alkylaryl and arylalkyl, and $(C_1-C_{10})$ alkyl-di$(C_6-C_{20})$aryl Si;

R' is selected from the group consisting of H, $(C_1-C_{10})$ alkyl, $(c_7-C_{20})$aroyl and $(C_2-C_{12})$acyl; and R''' is selected from the group consisting of halogen, $(C_1-C_{10})$alkoxyl, $(C_1-C_{10})$acyloxy, O-methane-sulfonyl and O-p-toluene sulfonyl.

Particularly preferred R and R' aroyls are benzoyl and naphthoyl as well as derivatives thereof.

Also particularly preferred are compounds where R is $(C_7-C_{20})$aroyl and $(C_{1-C10})$alkyl-diphenyl)Si. Still among the most preferred compounds are those where R''' is a halogen selected from the group consisting of fluorine, chlorine, bromine and iodine. Other preferred compounds are those wherein R' is $(C_1-C_{10})$alkyl or $(C_1-C_{12})$acyl.

Still another preferred group of compounds is that wherein R is $(C_7-C_{20})$aroyl and R' is $(C_1-C_{10})$alkyl or $(C_2-C_{12})$acyl The above compounds may be provided in pure form or as a composition of matter with other ingredients. Typically, the composition will comprise about 0.001 to 99.999 wt % of the compound, and more preferably about 0.1 to 99 wt %, and still more preferably about 1 to 75 wt % of the compound.

The compounds of formulas (a) and (b) of the invention, wherein R''' is a halogen may be prepared from compounds of similar formula, wherein R is as described, and R' is selected from the group consisting of $(C_1-C_{10})$alkyl, $(C_7-C_{20})$aroyl or $(C_2-C_{12})$acyl, all of which may be further substituted with O, S, N or alkyl as described herebelow. The conditions for this reaction are described below as part of the general scheme of the present method.

The compound of formula (b) wherein R''' is O-alkyl, O-acyl, O-methanesulfonyl and O-p-toluene sulfonyl may be prepared by methods known in the art starting from alcohols and reactive halo compounds.

The compound of the formula (a) shown above, wherein R is as described and R' is selected from the group consisting of $(C_1-C_{10})$alkyl, $(C_7-C_{20})$aroyl and $(C_2-C_{12})$acyl, may be prepared by methods known in the art. One possible method is the one described by Tann et al, J. Org. Chem. 50:3644 (1985).

The starting materials for the above method are compounds which are commercially available, and which through a simple scheme of preparation result in these compounds.

The composition of matter comprising the inventive compounds may be any composition obtained when synthesizing the compounds, in which case it is essentially a reaction mixture resulting therefrom.

Also part of this invention is a method of preparing a 2'-fluoro compound of the formula

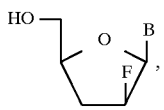

wherein B is selected from the group consisting of purines and pyrimidines, both of which may be substituted with halogen, $(C_1-C_{10})$alkyl, $(C_1-C_{12})$-haloalkyl, haloalkenyl and haloalkynyl, amino, hydroxy, hydroxylamino, aminoxy, $(C_1-C_{10})$alkoxy, oxygen, mercapto, $(C_1-C_{10})$alkylmercapto, $(C_6-C_{20})$aryl, $(C_7-C_{20})$ aryloxy, $(C_1-C_{10})$alkylamino, aza, and cyano, the method comprising (a) reacting a compound of the formula

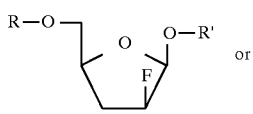

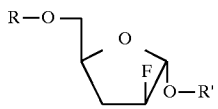

wherein

R is selected from the group consisting of H, $(C_7-C_{20})$ aroyl, $(C_6-C_{20})$aryl, arylalkyl and alkylaryl, and $(C_1-C_{10})$ alkyl-di$(C_6-C_{20})$aryl Si; and R' is selected from the group consisting of H, $(C_1-C_{10})$ alkyl, $(C_7-C_{20})$aroyl and $(C_2-C_{12})$-acyl, all of which may be further substituted with O, S, N or alkyl with an acid halide under conditions effective to obtain a halide of the formula

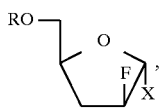

wherein X is selected from the group consisting of F, Cl, Br or I;

(b) adding thereto a silane of the formula

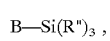

wherein

B is as defined above, and

R'' is, independent of one another, selected from the group consisting of $(C_1-C_{10})$alkyl, $(C_6-C_{20})$aryl, $(C_1-C_{10})$alkyl $(C_6C_{20})$aryl and $(C_6-C_{20})$aryl$(C_{1-C10})$alkyl under conditions effective to obtain a compound of the formula

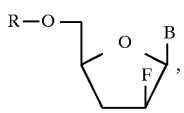

wherein R and B are as defined above; and (c) reacting the compound of formula (IV) with a reagent selected from the group consisting of ammonia, ammonia/methanol, $BCl_3$, $Bu_4NF$, sodium hydroxide and diisopropylamine under conditions effective to obtain the compound of formula (I).

Preferred (C_7–C_20)aryloxy is benzyloxy.

GENERAL SYNTHESIS SCHEME

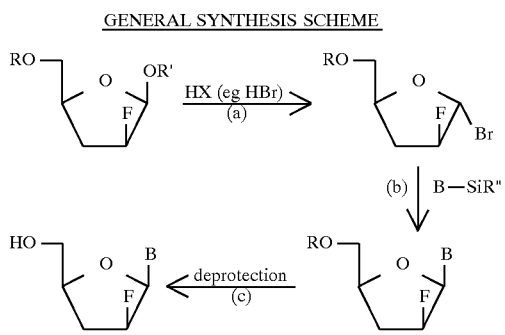

In general, the method is conveniently conducted at ambient temperature and pressure. However, broad ranges of temperatures and pressures may be utilized for each and one of the steps encompassed. Typically, step (a) may be conducted at a temperature of about 15° to 25° C. and preferably about 20° to 25° C., and a pressure of about 0.5 to 10 atm, and preferably about 1 atm.

The reaction of compound (II) with an acid halide is usually conducted in the presence of a solvent which either dissolves or suspends the compound of formula (II) and the acid halide. Other considerations in terms of this reaction are as follows.

The solvent is preferably a pure, organic, anhydrous, low-boiling point, non-nucleophilic solvent. By low boiling point is understood that the solvent has a boiling point of about 60° C. or lower. This facilitates its removal by flash evaporation. The solvent utilized for this step is typically an organic solvent that will not react with the halo compound and is preferably low-boiling. Examples of solvents are ether, dichloromethane and chloroform. However, others may also be utilized within the confines of this invention.

In general, in step (a) the molar equivalent ratio of the acid halide to the compound of formula (II) is about 10:1 to 4:1. However, other proportions may also be utilized.

The compound of formula (III) may or may not be isolated from the reaction mixture, as desired. Typically, when isolated, after the reaction solvent is removed, the compound of formula (III) may be separated from the reaction mixture by extraction into an organic solvent such as the organic phase of, e.g., a 10% $NaHCO_3/CH_2Cl_2$ mixture.

In step (a) Compound (II)a has been found to convert to compound (II)b in the presence of acid. It appears that compound (II)b is the one that actually reacts with the acid halide.

Step (b) is typically conducted at ambient temperature and pressure, but may also be conducted under a broad range of conditions such as about 15° to 25° C. of temperature, and preferably about 20° to 25° C., and a pressure of about 1 to 10 atm, and preferably about 1 atm.

The proportion of the compound B—Si(R")_3 to the compound of formula (III) is typically about 2:1 to 3:1, and preferably about 2:1.

This reaction may be conducted in the same solvent as the reaction of step (a), particularly when the compound of formula (III) is not separated from the mixture. However, other solvents that do not decompose themselves or do not interfere with the reaction or the stability of reactants and products may also be utilized.

The reaction of step (c) is typically conducted at ambient temperature and pressure. However, it may also be conducted under a broad range of temperatures and pressures such as about 15° to 25° C., and preferably about 20° to 25° C. and a pressure of about 1 to 10 atm, and preferably about 1 atm.

Typically, this reaction is conducted at a molar equivalent ratio of the reagent to the compound of formula (IV) of about 1:1 to 3:1, and preferably about 1.1:1.

The reaction of step (c) may be conducted without purifying the compound of formula (IV), that is, utilizing the same solvent and/or reaction mixture. However, if desired, the compound of formula (IV) may be purified, e.g., by silica gel chromatography.

The reagent employed in this step may typically be an organic solvent having a low boiling point. Examples are ammonia, ammonia/methanol, (n-Bu)_4NF, $BCl_3$, sodium hydroxide, diisopropylamine and Et_4NBF (Marquez et al, J. Med. Chem. 33(3):978 (1990); Tseng et al, J. Med. Chem. 32(7):1442(1989)).

In a further embodiment, the method of the invention may further comprise a step (d) encompassing separating the compound of formula (I) from the reaction mixture.

Typically, this separation is conducted by implementing known techniques. The compound may be separated by cooling the reaction mixture and separating it as a solid, by filtration or chromatography, and the like.

In a particularly desirable application, the method of the invention is applied to the preparation of 9-(2,3-dideoxy-2-fluoro-β-D-arabinofuranosyl)-purines and 1-(2,3-dideoxy-2-fluoro-β-D-arabinofuranosyl)-pyrimidines, and derivatives thereof such as those listed hereinbelow.

1-(2,3-Dideoxy-2-fluoro-β-D-arabinofuranosyl)-4-acetoxypyrimidin-2-one
1-(2,3-Dideoxy-2-fluoro-β-D-arabinofuranosyl)-4-fluoropyrimidin-2-one
1-(2,3-Dideoxy-2-fluoro-β-D-arabinofuranosyl)-4,5-difluoropyrimidin-2-one
1-(2,3-Dideoxy-2-fluoro-β-D-arabinofuranosyl)-4-chloropyrimidin-2-one
1-(2,3-Dideoxy-2-fluoro-β-D-arabinofuranosyl)-4-bromopyrimidin-2-one
1-(2,3-Dideoxy-2-fluoro-β-D-arabinofuranosyl)-4-iodopyrimidin-2-one
1-(2,3-Dideoxy-2-fluoro-β-D-arabinofuranosyl)-5-fluoropyrimidin-2-one
1-(2,3-Dideoxy-2-fluoro-β-D-arabinofuranosyl)-5-chloropyrimidin-2-one
1-(2,3-Dideoxy-2-fluoro-β-D-arabinofuranosyl)-5-bromopyrimidin-2-one
1-(2,3-Dideoxy-2-fluoro-β-D-arabinofuranosyl)-5-iodopyrimidin-2-one
1-(2,3-Dideoxy-2-fluoro-β-D-arabinofuranosyl)-cytosine
1-(2,3-Dideoxy-2-fluoro-β-D-arabinofuranosyl)-uracil
1-(2,3-Dideoxy-2-fluoro-β-D-arabinofuranosyl)-5-fluorocytosine
1-(2,3-Dideoxy-2-fluoro-β-D-arabinofuranosyl)-5-fluorouracil
1-(2,3-Dideoxy-2-fluoro-β-D-arabinofuranosyl)-5-chlorocytosine
1-(2,3-Dideoxy-2-fluoro-β-D-arabinofuranosyl)-5-chlorouracil
1-(2,3-Dideoxy-2-fluoro-β-D-arabinofuranosyl)-5-bromocytosine
1-(2,3-Dideoxy-2-fluoro-β-D-arabinofuranosyl)-5-bromouracil
1-(2,3-Dideoxy-2-fluoro-β-D-arabinofuranosyl)-5-iodocytosine
1-(2,3-Dideoxy-2-fluoro-β-D-arabinofuranosyl)-5-iodouracil 1-(2,3-Dideoxy-2-fluoro-β-D-arabinofuranosyl)-5-methylcytosine
1-(2,3-Dideoxy-2-fluoro-β-D-arabinofuranosyl)-5-methyluracil
1-(2,3-Dideoxy-2-fluoro-β-D-arabinofuranosyl)-5-ethylcytosine
1-(2,3-Dideoxy-2-fluoro-β-D-arabinofuranosyl)-5-ethyluracil
1-(2,3-Dideoxy-2-fluoro-β-D-arabinofuranosyl)-5-(bromovinyl)cytosine
1-(2,3-Dideoxy-2-fluoro-β-D-arabinofuranosyl)-5-(bromovinyl)uracil
1-(2,3-Dideoxy-2-fluoro-β-D-arabinofuranosyl)-5-(trifluoromethyl)-cytosine
1-(2,3-Dideoxy-2-fluoro-β-D-arabinofuranosyl)-5-(trifluoromethyl)-uracil
1-(2,3-Dideoxy-2-fluoro-β-D-arabinofuranosyl)-pyrimidin-2-one
1-(2,3-Dideoxy-2-fluoro-β-D-arabinofuranosyl)-4-(hydroxylamino)pyrimidin-2-one
1-(2,3-Dideoxy-2-fluoro-β-D-arabinafuranosyl)-4-(aminooxy)pyrimidin-2-one
1-(2,3-Dideoxy-2-fluoro-β-D-arabinofuranosyl)-4-methoxypyrimidin-2-one
9-(2,3-Dideoxy-2-fluoro-β-D-arabinofuranosyl)-purine
9-(2,3-Dideoxy-2-fluoro-β-D-arabinofuranosyl)-6-aminopurine
9-(2,3-Dideoxy-2-fluoro-β-D-arabinofuranosyl)-6-hydroxypurine
9-(2,3-Dideoxy-2-fluoro-β-D-arabinofuranosyl)-6-fluoropurine
9-(2,3-Dideoxy-2-fluoro-β-D-arabinofuranosyl)-6-chloropurine
9-(2,3-Dideoxy-2-fluoro-β-D-arabinofuranosyl)-6-bromopurine
9-(2,3-Dideoxy-2-fluoro-β-D-arabinofuranosyl)-6-iodopurine
9-(2,3-Dideoxy-2-fluoro-β-D-arabinofuranosyl)-6-(methylamino)purine
9-(2,3-Dideoxy-2-fluoro-β-D-arabinofuranosyl)-6-(dimethylamino)purine
9-(2,3-Dideoxy-2-fluoro-β-D-arabinofuranosyl)-6-(trifluoromethyl-amino)purine
9-(2,3-Dideoxy-2-fluoro-β-D-arabinofuranosyl)-6-(benzoylamino)purine
9-(2,3-Dideoxy-2-fluoro-β-D-arabinofuranosyl)-6-(acetylamino)purine
9-(2,3-Dideoxy-2-fluoro-β-D-arabinofuranosyl)-6-(hydroxylamino)purine
9-(2,3-Dideoxy-2-fluoro-β-D-arabinofuranosyl)-6-(aminooxy)purine
9-(2,3-Dideoxy-2-fluoro-β-D-arabinofuranosyl)-6-methoxypurine
9-(2,3-Dideoxy-2-fluoro-β-D-arabinofuranosyl)-6-acetoxypurine
9-(2,3-Dideoxy-2-fluoro-β-D-arabinofuranosyl)-6-(benzoyloxy)purine
9-(2,3-Dideoxy-2-fluoro-β-D-arabinofuranosyl)-6-methylpurine
9-(2,3-Dideoxy-2-fluoro-β-D-arabinofuranosyl)-6-ethylpurine
9-(2,3-Dideoxy-2-fluoro-β-D-arabinofuranosyl)-6-(trifluoromethyl)-purine
9-(2,3-Dideoxy-2-fluoro-β-D-arabinofuranosyl)-6-phenylpurine
9-(2,3-Dideoxy-2-fluoro-β-D-arabinofuranosyl)-6-mercaptopurine
9-(2,3-Dideoxy-2-fluoro-β-D-arabinofuranosyl)-6-(methylmercapto)-purine
9-(2,3-Dideoxy-2-fluoro-β-D-arabinofuranosyl)-6-aminopurine-1-oxide
9-(2,3-Dideoxy-2-fluoro-β-D-arabinofuranosyl)-6-hydroxypurine-1-oxide
9-(2,3-Dideoxy-2-fluoro-β-D-arabinofuranosyl)-2-amino-6-hydroxypurine
9-(2,3-Dideoxy-2-fluoro-β-D-arabinofuranosyl)-2,6-diaminopurine
9-(2,3-Dideoxy-2-fluoro-β-D-arabinofuranosyl)-2-amino-6-chloropurine
9-(2,3-Dideoxy-2-fluoro-β-D-arabinofuranosyl)-2-amino-6-bromopurine
9-(2,3-Dideoxy-2-fluoro-β-D-arabinofuranosyl)-2-amino-6-iodopurine
9-(2,3-Dideoxy-2-fluoro-β-D-arabinofuranosyl)-2-amino-6-fluoropurine
9-(2,3-Dideoxy-2-fluoro-β-D-arabinofuranosyl)-2-aminopurine
9-(2,3-Dideoxy-2-fluoro-β-D-arabinofuranosyl)-2-amino-6-mercapto-purine
9-(2,3-Dideoxy-2-fluoro-β-D-arabinofuranosyl)-2-amino-6-(methylmercapto)purine
9-(2,3-Dideoxy-2-fluoro-β-D-arabinofuranosyl)-2-amino-6-(hydroxyl-amino)purine
9-(2,3-Dideoxy-2-fluoro-β-D-arabinofuranosyl)-2-amino-6-methoxypurine
9-(2,3-Dideoxy-2-fluoro-β-D-arabinofuranosyl)-2-amino-6-ethoxypurine
9-(2,3-Dideoxy-2-fluoro-β-D-arabinofuranosyl)-2-amino-6-(benzoyloxy)-purine
9-(2,3-Dideoxy-2-fluoro-β-D-arabinofuranosyl)-2amino-6-acetoxypurine
9-(2,3-Dideoxy-2-fluoro-β-D-arabinofuranosyl)-2-amino-6-(aminooxy)-purine
9-(2,3-Dideoxy-2-fluoro-β-D-arabinofuranosyl)-2-amino-6-methylpurine
9-(2,3-Dideoxy-2-fluoro-β-D-arabinofuranosyl)-2-amino-6-phenylpurine
9-(2,3-Dideoxy-2-fluoro-β-D-arabinofuranosyl)-6-amino-8-bromopurine
9-(2,3-Dideoxy-2-fluoro-β-D-arabinofuranosyl)-6-amino-3-deazapurine
9-(2,3-Dideoxy-2-fluoro-β-D-arabinofuranosyl)-6-amino-8-azapurine
9-(2,3-Dideoxy-2-fluoro-β-D-arabinofuranosyl)-2-amino-6-hydroxy-8-azapurine
9-(2,3-Dideoxy-2-fluoro-β-D-arabinofuranosyl)-6-amino-7-deazapurine
9-(2,3-Dideoxy-2-fluoro-β-D-arabinofuranosyl)-2-methyl-6-aminopurine
9-(2,3-Dideoxy-2-fluoro-β-D-arabinofuranosyl)-6-cyanopurine
9-(2,3-Dideoxy-2-fluoro-β-D-arabinofuranosyl)-8-methyl-6-aminopurine
9-(2,3-Dideoxy-2-fluoro-β-D-arabinofuranosyl)-2-methyl-6-(methyl-amino)purine The tribenzoatefluoroarabinose (compound 1) utilized in the examples as a starting material may not be commercially available. It may be synthesized, however, by applying technology known in the art as, for example, the method described by Tann et al (Tann et al, J. Org. Chem. 50:3644 (1985)).

The compounds described herein have the purine or pyrimidine base at C-1' on the β configuration (upward).

The following examples illustrate a few representative embodiments of the compound and process according to this invention, and are set forth to teach those skilled in the pertinent art how to practice this invention but are not to be construed as limiting in scope. All parts and percentages are by weight and temperatures are in degrees C unless otherwise specified.

EXAMPLES

The following scheme is provided to accompany the text of the examples and it encompasses all the reactions described therein as well as the different compounds by number.

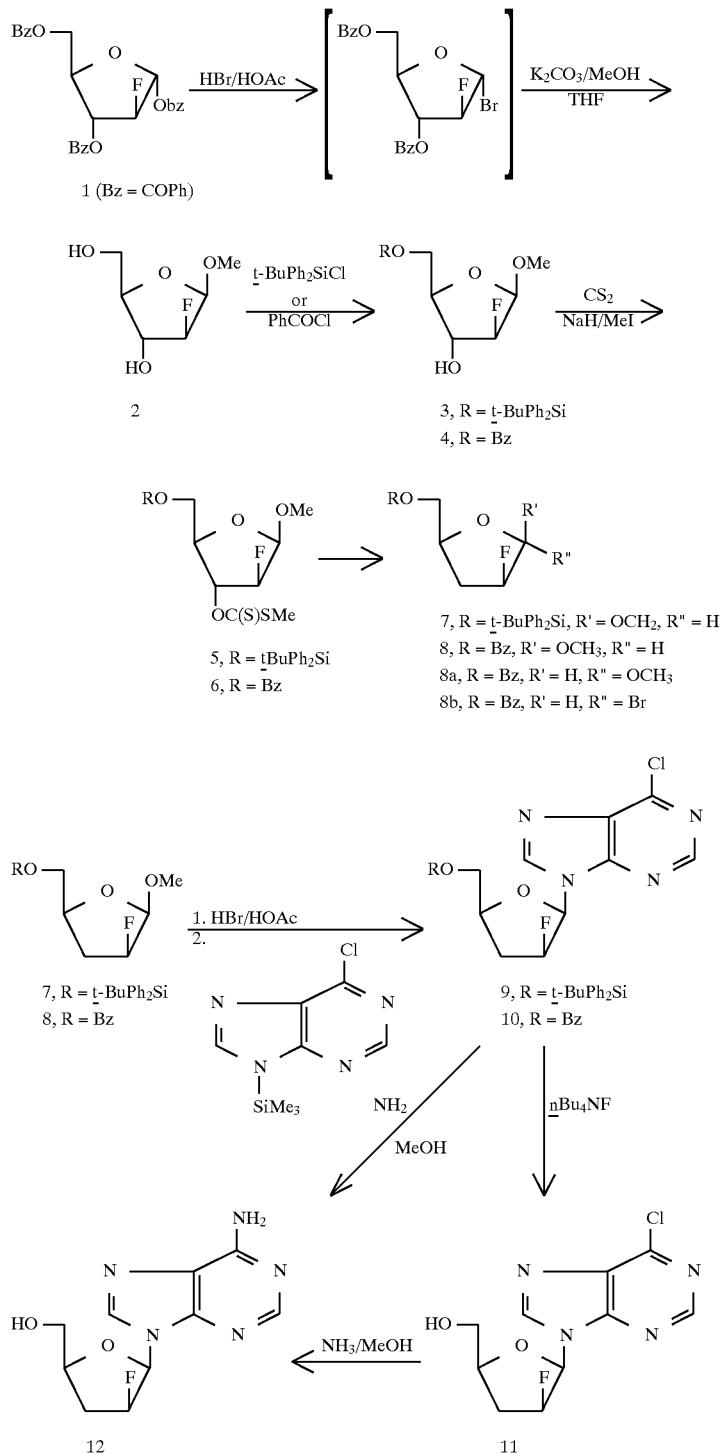

-continued

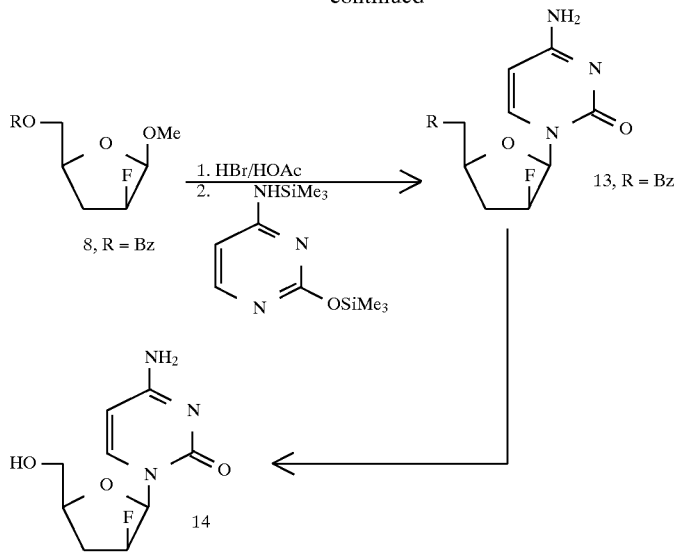

Example 1

1-0-methyl-3,5-dihydroxy-2-deoxy-2-fluoro-β-D-arabinofuranose (2)

To a solution of the 1,3,5-tri-O-benzoyl-2-deoxy-2-fluoro-α-D-arabinofuranose 1 (6.78 g; 14.6 mmol) in dry $CH_2Cl_2$ (20 ml) was added 4.1M solution of HBr in acetic acid (8 ml; 32.8 mmol) at room temperature.

After 24 hours of stirring, the reaction mixture was worked up to give 5.99 g (97.1%) of the intermediate bromosugar as a thick oil. This oil was used in the next step without further purification.

To a solution of the bromosugar intermediate (5.99 g; 14.1 mmol) in dry tetrahydrofuran (THF, 10 ml) was added $CH_3OH$ (40 ml) and anhydrous $K_2CO_3$ (4.22 g; 32.4 mmol).

The mixture was stirred at room temperature for 36 hours and then worked up. The crude product was purified by flash column chromatography (Silica gel, EtOAc-hexane (0–100%)) to yield 1.556 g (64.3%) of 2 as an oil. The properties of the product are as follows.

NMR ($CDCl_3$) δ 3.50 (s, 3, OMe), 3.70 (m, 2, H-5'$_{a,b}$), 3.95 (m, 1, H-4'), 4.60(dt,J=20 HZ, J'=8 Hz, 1, H-3'), 4.86 (dm, J=52 Hz, 1, H-2'), 4.90 (d, J=2 Hz, H-1').

Example 2

1-0-methyl-5-0-(tert-butyldiphenylsilyl)-2-deoxy-2-fluoro-3-hydroxy-β=D -arabinofuranose (3)

To a solution of the dihydroxysugar 2 (0.515 g; 3.10 mmol) and imidazole (0.630 g; 9.25 mmol) in dry DMF (10 ml) was added tert-butyl diphenyl chlorosilane (895 μl, 0.957 g; 3.48 mmol). The reaction mixture was stirred at room temperature under nitrogen atmosphere for 3 hours.

The residue obtained after evaporation under vacuum was purified by flash column chromatography silica gel, EtOAc:hexane (10–25%) to yield 0.919 g (73.5%) of the desired product 3 as an oil.

The characteristics of the product are as follows.

NMR ($CDCl_3$) δ 1.10 (s, 9, Me), 3.30 (s, 1, OMe), 3.80 (m, 2, H-5'$_{a,b}$), 3.95 (m, 1, H-4'), 4.55 (dt, J=20 Hz, J'=6 Hz, H-3'), 4.86 (dm, J=50 Hz, 1, H-2'), 4.88 (d, J=6 Hz, H-1'), 7.30–7.80 (m, 10, Ph).

Example 3

1-0-methyl-5-0-benzoyl-2-deoxy-2-fluoro-3-hydroxy-β-D-arabinofuranose (4)

A solution of the dihydroxy sugar 2 (1.28 g; 7.70 mmol) in dry purine (20 ml) was cooled to −30° C. under a nitrogen atmosphere.

To this mixture, a solution of benzoyl chloride (0.89 ml; 7.66 mmol) in dry $CH_2Cl_2$ (10 ml) was added over a period of 15 minutes. The temperature was maintained between −30° C. to −10° C. and the reaction mixture was stirred at this temperature for 45 minutes.

Removal of the solvent in vacuo was followed by flash column chromatography of the residue (silica gel, MeOH:$CH_2Cl_2$ (0–5%)) to yield compound 4 as an oily material (1.41 g, 67.9%).

The characteristics of the compound are as follows.

NMR ($CDCl_3$) δ 3.40 (s, 1, OMe), 4.15 (m, 1, H-4'), 4.30–5.20 (m, 4, H-5'$_{a,b}$, H-2', H-3'), 4.90 (d, J=6 Hz, H-1'), 7.40–8.20 (m, 5, Ph).

Example 4

1-0-methyl-5-0-(tert-butyldiphenylsilyl)-3-)-(S-methyldithiocarbonyl) -2-deoxy-2-fluoro-β-D-arabinofuranose (5)

To a solution of the tert-butyl diphenylsilyl ether 3 (0.805 g; 1.99 mmol) in dry DMF (10 ml) was added carbon disulfide (0.70 ml, 0.88 g, 11.64 mmol). The mixture was stirred for 15 minutes while cooling over an ice bath. Sodium hydride, has dispersed in mineral oil (0.17 g; 73 mmol), and then added to the mixture. After 30 minutes, methyl iodide (1.45 ml, 3.30 g; 23.2 mmol) was introduced to the reaction and the resulting mixture was stirred over an ice-bath for 10 minutes, and then allowed to reach room temperature.

After 30 minutes the solvent was removed and the residue was purified by flash column chromatography (silica gel, EtOAc:hexane (0–10%)) to give 0.384 g (89.8%) of the desired product 5 as an oil.

The characteristics of the product are as follows.

NMR ($CDCl_3$) δ 1.00 (s, 9, Me), 2.55 (s, 1, SMe), 3.40 (s, 1, OMe), 3.90 (m, 2, H-5'$_{a,b}$), 4.15 (m, 1, H-4'), 5.00–5.35

(m, 2, H-2', H-1'), 6.40 (dt, J=16 Hz, J'=4 Hz, H-3'), 7.30–7.80 (m, 10, Ph).

Example 5

1-0-methyl-5-0-(tert-butyldiphenylsilyl)-2,3-dideoxy-2-fluoro-β-D-arabinofuranose (7)

To a solution of xanthate 5 (0.875 g; 1.77 mmol) in dry toluene (10 ml) was added AIBN (0.50 g; 0.3 mmol). The mixture was stirred at room temperature under a nitrogen atmosphere for 15 minutes and then tributyltin hydride (1.05 ml, 1.13 g; 3.90 mmol) was added. The reaction mixture was heated at reflux for 1 hour. The mixture was cooled. After evaporation of the solvent, the residue was purified by flash column chromatography (silica gel, EtOAc:hexane (0–10%)) to give 0.587 g (85.6%) of the desired product 7 as an oil: NMR (CDCl$_3$) δ 1.00 (s, 9, Me), 2.00–2.50 (m, 2, H-3'), 3.40 (s, 1, OMe), 3.70 (m, 2, H-5'$_{a,b}$), 4.20 (APPARENT Q, J=4 Hz, 1, H-4'), 4.80–5.20 (M, 2, H-2', H-1'), 7.30–7.80 (M, 10, Ph).

Example 6

1-0-methyl-5-0-benzoyl-2,3-dideoxy-2-fluoro-β-D-arabinofuranose (8)

Compound 8 was prepared in exactly the same manner as compound 7 but starting from xanthate 6. The characteristics of the product obtained are as follows.

NMR (CDCl$_3$) δ 2.00–2.50 (m, 2, H-3'$_{a,b}$),3.40 (s, 1, OMe), 4.40 (m, 3, H-4', H-5'$_{a,b}$), 4.90 (m, 1.5, H-1'and half of H-2'), 5.20 (m, 0.5, half of H-2'), 7.50 (m, 3, Ph), 8.10 (m, 2, Ph).

Example 7

6-chloro-9-(5-0-benzoyl-2,3-dideoxy-2-fluoro-β-D-arabinofuranosyl)-9H-purine (10)

a) Silylation of 6-chloropurine

A mixture of 6-chloropurine (155 mg, 1.0 mmol, 2.1 equiv) in hexamethyldisilazane (10 ml) was treated with a few crystals of ammonium sulfate and warmed at reflux under nitrogen.

After 1.5 hrs., volatiles were distilled from the homogeneous reaction solution and the resultant yellow solid was cooled to room temperature and dried under vacuum.

b) Preparation of 1-bromo 5-0-benzoyl-2,3-dideoxy-2-fluoro-α-D-arabinofuranose (8b)

A solution of 1-0-methyl-5-0-benzoyl-2,3-dideoxy-2-fluoro-β-arabinofuranose (8, 116 mg, 0.46 mmol) in dichloromethane (10 ml) was treated with an acetic acid solution of hydrogen bromide (4.1M, 0.6 ml, 2.36 mmol, 5.2 equiv) and stirred at 23° C. under nitrogen.

This resulted initially in the rapid epimerization of the 1'-anomeric carbon atom giving 1-0-methyl-5-0-benzoyl-2,3-dideoxy-2-fluoro-α-D-arabinofuranose (8a) as an intermediate, which could be but was not normally isolated.

The characteristics of the product are as follows.

NMR of 8a (CDCl$_3$) δ 2.00 (m, 1, H-3'$_β$), 2.50 (m, 1, H-3'$_α$), 3.35 (s, 3, OMe), 4.40 (m, H-5'$_{a,b}$,H-4'), 5.00 (dd, J=54 Hz, J'=6 Hz, 1, H-2'), 5.20 (d, J=14 Hz, 1, H-1'), 7.50 (m, 3, Ph), 8.20 (m, 2, Ph).

Under these conditions, the compound 8a was converted to 1-bromo-5-0-benzoyl-2,3-dideoxy-2-fluoro-α-D-arabinofuranose (8b) which could be, but was not normally, isolated before addition of the silylated base.

The characteristics of the compound are as follows.

NMR of 8b (CDCl$_3$) δ 2.00 (m, 1, H-3'$_β$), 2.60 (m, 1, H-3'$_α$), 4.40 (m, 2, H-5'$_{a,b}$), 4.70 (m, 1, H-4'), 5.00 (dd, J=54 Hz, J'=6 Hz, 1, H-2'), 5.60 (d, J=14 Hz, 1, H-1'), 7.50 (m, 3, Ph), 8.20 (m, 2, Ph).

After 1 hr., the solution was concentrated under high vacuum and the residue dissolved in dichloromethane (75 ml) and washed with water (2×50 ml) and saturated NaHCO$_3$ (2×50 ml). The organic layer was dried (MgSO$_4$) and concentrated under high vacuum to give the desired bromosugar as an oil. This oil was used directly in the condensation reaction.

C) Condensation step

A solution of the freshly silylated 6-chloropurine in acetonitrile (3 ml) was poured onto the crude bromosugar and stirred to homogeneity.

The reaction mixture was treated with 4A molecular sieves (8–12 mesh) and stirred at 23° C. overnight and then filtered through a short column of silica gel (2 cm×2 cm, ethyl acetate eluant).

The filtrate was concentrated in vacuo. Flash chromatography (SiO$_2$, 1.0 cm×12 cm, 40% ethyl acetate-light petroleum ether eluant) yielded 6-chloro-9-(5-0-benzoyl-2,3-dideoxy-2-fluoro-βD-arabinofuranosyl)-9-H-purine (35 mg, 20%) as a white solid.

The characteristics of the product are as follows.

$^1$H NMR (200 MHz, CDCl$_3$) δ 8.73 (s, 1, H-2), 8.45 (d, 1, J=2.7 Hz, H-8), 8.08 (d, 2, J=7.0 Hz, benzoyl C2-H), 7.63–7.41 (m, 3, benzoyl C3-H, C4-H), 6.44 (dd, 1, J=19.7, 2.8 Hz, H-1'), 5.34 (dm, 1, J=53 Hz, H-2'), 4.72–4.55 (m, 3, H-4', H-5'), 2.83–2.43 (m, 2, H-3').

Example 8

6-chloro-9-(5-0-(tert-butyldiphenyl)silyl-2, 3-dideoxy-2-fluoro-β-D-arabinofuranosyl)-9H-purine (9).

A solution of 1-0-methyl-5-0-(tert-butyl diphenyl)silyl-2,3-didoxy-2-fluoro-β-D-arabinofuranose (7, 455 mg; 1.17 mmol) in dichloromethane (10 ml) was treated with an acetic acid solution of hydrogen bromide (4.1M, 0.55 ml, 2.26 mmol, 1.9 equiv) and stirred at 23° C. After 1 hr., volatiles were removed in vacuo and the residue was dried under vacuum for 0.5 hours.

The silylated 6-chloropurine (from 6-chloropurine, acetonitrile (3 ml), poured onto the crude bromosugar and stirred at 60° C. overnight. After 15 hours, volatiles were removed in vacuo and flash chromatography of the residue (SiO$_2$, 2.1 cm×19 cm, 15–30% ethyl acetate-light petroleum ether eluant) yielded the product (68 mg, 13% as a white solid.

The characteristics of the product are as follows.

$^1$H NMR (200 MHz, CDCl$_3$) δ 8.73 (s, 1, H-2), 8.36 (d, 1, J=2.5 Hz, H-8), 7.71–7.39 (m, 10, Ph), 6.37 (dd, I, J=18, 3.2 Hz, H-1'), 5.29 (dm, 1, J=53 Hz, H-2'), 4.36 (apparent q, 1, J=5.6 Hz, H-4'), 3.87 (m, 2, H-5'), 2.61 (m, 1, H-3'), 2.46 (m, 1, H-3'), 1.08 (s, 9, tC$_4$H$_9$).

Example 9

6-chloro-9-(2,3-dideoxy-2-fluoro-β-D-arabinofuranosyl)-9H-purine (11)

A solution of 6-chloro-9-(5-0-tert-butyldiphenylsilyl-2,3-dideoxy-2-fluoro-β-D-arabinofuranosyl)-9H-purine (9, 80 mg, 0.16 mmol) in tetrahydrofuran (2 mL) was treated with a tetrahydrofuran solution of tetrabutylammonium fluoride (1.0M, 0.2 mL, 0.2 mmol, 1.3 equiv) and stirred at 23° C. After 30 minutes, the reaction mixture was concentrated in vacuo. Flash chromatography (SiO$_2$, 1.1 cm×12 cm, ethyl acetate eluent) provided the product 31 mg, 73%) as a white solid.

The characteristics of the product are as follows.

$^1$H NMR (200 MHz, methanol-d$_4$) δ 8.73 (d, 1, J=2.0 Hz, H-8), 8.64 (s, 1, H-2), 6.42 (dd, 1, J=18.0, 3.0 Hz, H-1'), 5.36 (ddt, 1, J=53, 3.0, 2.0 Hz, H-2'), 4.27 (m, 1, H-4'), 3.69 (m, 2, H-5'), 2.70–2.30 (m, 2, H-3').

Example 10

6-amino-9-(2,3-dideoxy-2-fluoro-β-D-arabinofuranosyl)-9H-purine (12)

A solution of 6-chloro-9-(2,3-dideoxy-2-fluoro-β-D-arabinofuranosyl)-9H-purine (16 mg, 0.059 mmol) in saturated methanolic ammonia (5 ml) was sealed in a glass tube under an atmosphere of ammonia.

The reaction solution was warmed at 105° C. in an oil-bath. After 48 hours, the reaction was cooled in an ice bath.

The reaction solution was transferred to a round-bottom flask and concentrated in vacuo. The resultant solid was dried under vacuum to yield the fluoronucleoside (14.8 mg, 99%).

This material was identical to the authentic material by $^1$H NMR (Marquez, et al, Biochem. Pharmacol., 36, 2719 (1987)).

Example 11

1-(6-0-benzoyl-2,3-dideoxy-2-fluoro-β-D-arabinofuranosyl)cytosine (13)

Cytosine (0.135 g, 1.21 mmol, 3 equiv) was silylated with bis(trimethylsilyl)trifluoroacetamide (2 ml). A solution of the silylated cytosine in dry 1,2-dichloroethane (10 ml) was added to a freshly prepared solution of 5-0-benzoyl-1-bromo-2,3-dideoxy-2-fluoro-α-β-D-arabinofuranose (0.393 mmol, vide supra) in 1,2-dichloroethane (5 ml), and the mixture was refluxed for 4 hours under nitrogen.

Methanol was added (10 ml) and the suspension was filtered through a pad of Celite. The filtrate was concentrated under vacuum and the residual material was purified by preparative thin layer chromatography (TLC), Analtech 2000μ, methylene chloride/MeOH, 9:1).

Two bands were separated.

The major band (Rf=0.35, 0.081 g, 62%) corresponded to the desired compound (13). The minor band (Rf=0.28, 0.011 g, 8.4%) was identified as the α-anomer.

Compound 13 was recrystallized from CH$_2$Cl$_2$/ether to give a tan solid of the following characteristics.

mp 149.5°–151° C.;

NMR (200 MHz, MeOH-d$_4$) δ 2.00–2.80 (m, 2, H-3'), 4.50 (m, 3, H-4', H-5), 5.20 (dm, 1, J=53 Hz, H-2'), 5.70 (d, 1, J=7.5 Hz, H-5), 5.95 (dd, 1, J=19.5 Hz, J=2.8 Hz, H-1'), 7.30–8.00 (m, 6, H-6, aromatic).

Example 12

1-(2,3-dideoxy-2-fluoro-β-D-arabinofuranosyl) cytosine (14)

Treatment of 13 with methanolic ammonia at room temperature in a pressure bottle for 16 hours afforded, after the conventional workup, a sample of compound 14 that was identical to a sample of this material prepared by a different approach. Also the physical and spectral constants were identical to those reported in the literature for this compound (van Aershot A. et al, J. Med. Chem. 32:1743 (1989)).

The invention now being fully described, it will be apparent to one of ordinary skill in the art that many changes and modifications can be made thereto without departing from the scope of the invention as set forth herein.

We claim:

1. A method of preparing a 2'-fluoro compound of the formula

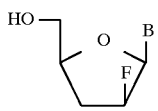    (I)

wherein B is selected from the group consisting of purines and pyrimidines, both of which may be substituted with at least one substituent selected from the group consisting halogen, (C$_1$–C$_{10}$)alkyl, (C$_1$–C$_{12}$)-haloalkyl, (C$_2$–C$_{12}$) haloalkenyl, (C$_2$–C$_{12}$) haloalkynyl, amino, hydroxy, hydroxylamino, aminoxy, (C$_1$–C$_{10}$)alkoxy, mercapto, (C$_1$–C$_{10}$)alkylmercapto, (C$_6$–C$_{20}$)aryl, (C$_7$–C$_{20}$)aryloxy, (C$_1$–C$_{10}$)alkylamino, aza, and cyano, the method comprising (a) reacting a compound selected from the group consisting of formulas II(a) and II(b)

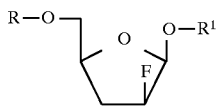    (IIa)

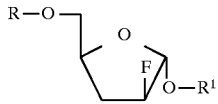    (IIb)

wherein

R is selected from the group consisting of H, (C$_7$–C$_{20}$) aroyl, (C$_6$–C$_{20}$)aryl, (C$_7$–C$_{20}$) alkylaryl, (C$_7$–C$_{20}$) arylalkyl, and (C$_1$–C$_{10}$)alkyl-di(C$_6$–C$_{20}$)aryl Si; and R' is selected from the group consisting of H, (C$_1$–C$_{10}$) alkyl, (C$_7$–C$_{20}$)aroyl and (C$_2$–C$_{12}$)acyl, all of which may be further substituted with at least one substituent selected from the group consisting of O, S, N and alkyl, with an acid halide to obtain a halide of the formula

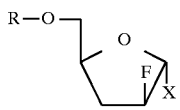    (III)

wherein X is selected from the group consisting of F, Cl, Br and (b) adding thereto a silane of the formula

wherein

B is as defined above, and each R" is, independent of one another, selected from the group consisting of (C$_1$–C$_{10}$) alkyl, (C$_6$–C$_{20}$)aryl, (C$_1$–C$_{10}$)alkyl(C$_6$–C$_{20}$)aryl and (C$_6$–C$_{20}$)aryl(C$_1$–C$_{10}$)alkyl, to obtain a compound of the formula

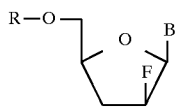

(IV)

wherein R and B are as defined above; and (c) reacting the compound of formula (IV) with a reagent selected from the group consisting of ammonia, ammonia/methanol, $BCl_3$, $Bu_4NF$, sodium hydroxide and diisopropylamine to obtain the compound of formula (I).

2. The method of claim 1, further comprising (d) separating the compound of formula (I) from the reaction mixture.

3. The method of claim 1, wherein steps (a), (b) and (c) are conducted in a solvent selected from the group consisting of methanol, tetrahydrofuran and methylene chloride.

4. The method of claim 1, wherein the reagent of step (c) is selected from the group consisting of ammonia, $Bu_4NF$ and $BCl_3$.

5. The method of claim 2, wherein step (d) is conducted by a technique selected from the group consisting of solvent extraction, chromatography and filtration.

6. The method of claim 1, wherein

B of formula (I) is selected from the group consisting of cytosine, uracil, 5-fluorocytosine, 5-fluorouracil, 5-chlorocytosine, 5-chlorouracil, 5-bromocytosine, 5-bromouracil, 5-iodocytosine, 5-iodouracil, 5-methylcytosine, 5-methyluracil, 5-ethylcytosine, 5-ethyluracil, 5-(bromovinyl)cytosine, 5-(bromovinyl)uracil, 5-(trifluoro methyl)cytosine, 5-(trifluoromethyl) uracil, pyrimidin-2-one, 4-(hydroxylamino)pyrimidin-2-one, 4-(aminooxy)pyrimidin-2-one, 4-methoxypyrimidin-2-one, 4-acetoxypyrimidin-2-one, 4-fluoropyrimidin-2-one, 4,5-difluoropyrimidin-2-one, 4-chloropyrimidin-2-one, 4-bromopyrimidin-2-one, 4-iodopyrimidin-2-one, 5-fluoropyrimidin-2-one, 5-chloropyrimidin-2-one, 5-bromopyrimidin-2-one, 5-iodopyrimidin-2-one, purine, 6-aminopurine, 6-hydroxypurine, 6-fluoropurine, 6-chloropurine, 6-bromopurine, 6-iodopurine, 6-(methylamino)purine, 6-(dimethylamino)purine, 6-(trifluoromethyl-amino)purine, 6-(benzoylamino)purine, 6-(acetylamino)purine, 6-(hydroxylamino)purine, 6-(aminooxy)purine, 6-methoxypurine, 6-acetoxypurine, 6-(benzoyloxy)purine, 6-methylpurine, 6-ethylpurine, 6-(trifluoromethyl)purine, 6-phenylpurine, 6-mercaptopurine, 6-(methylmercapto)-purine, 6-aminopurine-1-oxide, 6-hydroxypurine-1-oxide, 2-amino-6-hydroxypurine, 2,6-diaminopurine, 2-amino-6-chloropurine, 2-amino-6-bromopurine, 2-amino-6-iodopurine, 2-amino-6-fluoropurine, 2-aminopurine, 2-amino-6-mercaptopurine, 2-amino-6-(methylmercapto)purine, 2-amino-6-(hydroxylamino)purine, 2-amino-6-methoxypurine, 2-amino-6-ethoxypurine, 2-amino-6-(benxoyloxy)purine, 2-amino-6-acetoxypurine, 2-amino-6-(aminooxy)purine, 2-amino-6-methylpurine, 2-amino-6-phenylpurine, 6-amino-8-bromopurine, 6-amino-3-deazapurine, 6-amino-8-azapurine, 2-amino-6-hydroxy-8-azapurine, 6-amino-7-deazapurine, 2-methyl-6-aminopurine, 6-cyanopurine, 8-methyl-6-aminopurine and 2-methyl-6-(methylamino)purine.

* * * * *